United States Patent [19]

Legrow et al.

[11] Patent Number: 5,380,527
[45] Date of Patent: Jan. 10, 1995

[54] ALKYLMETHYLSILOXANE MIXTURES FOR SKIN CARE

[75] Inventors: Gary E. Legrow; Regina M. Malczewski, both of Midland, Mich.

[73] Assignee: Dow Corning Corporation, Midland, Mich.

[21] Appl. No.: 750,136

[22] Filed: Aug. 26, 1991

[51] Int. Cl.$^6$ .............................................. A61K 7/02
[52] U.S. Cl. ..................... 424/401; 424/59; 424/63; 514/844; 514/846; 514/847
[58] Field of Search ............... 424/401, 59, 63, 78; 514/847, 844, 846

[56] References Cited

U.S. PATENT DOCUMENTS

| | | | |
|---|---|---|---|
| 4,574,082 | 3/1986 | Tietjen | 424/63 |
| 4,973,476 | 11/1990 | Krzysik | 424/71 |
| 4,980,167 | 12/1990 | Harashima et al. | 424/401 |
| 5,035,890 | 7/1991 | Braun | 424/401 |

FOREIGN PATENT DOCUMENTS 737134  5/1983  United Kingdom .

OTHER PUBLICATIONS

Th. Goldschmidt Ag. ABIL(R) Silicones.

*Primary Examiner*—Thurman K. Page
*Assistant Examiner*—Amy Hulina
*Attorney, Agent, or Firm*—Roger E. Gobrogge

[57] ABSTRACT

This invention relates to alkylmethylsiloxanes mixtures which are useful for softening and moisturizing skin. The mixtures comprise one or more alkylmethylsiloxane solvents of the structure $[MeRSiO]_a[Me_2SiO]_b$ or $R'Me_2SiO(MeRSiO)_w(Me_2SiO)_xSiR'Me_2$ and one or more alkylmethylsiloxane waxes of the structure $R'Me_2SiO(Me_2SiO)_y(MeRSiO)_zSiMe_2R'$, wherein each R is independently a hydrocarbon of 6 to 30 carbon atoms, R' is methyl or R, a is 1–6, b is 0–5, w is 0–5 and x is 0–5, provided a+b is 3–6 and w is not 0 if R' is methyl.

6 Claims, No Drawings

ALKYLMETHYLSILOXANE MIXTURES FOR SKIN CARE

BACKGROUND OF THE INVENTION

This invention relates to alkylmethylsiloxane mixtures which are useful for softening and moisturizing skin. The mixtures comprise one or more alkylmethylsiloxane solvents of the structure [MeRSiO]$_a$[Me$_2$SiO]$_b$ or R'Me$_2$SiO(MeRSiO)$_w$(Me$_2$SiO)$_x$SiR'Me$_2$ and one or more alkylmethylsiloxane waxes of the structure R'Me$_2$SiO(Me$_2$SiO)$_y$(MeRSiO)$_z$SiMe$_2$R', wherein each R is independently a hydrocarbon of 6 to 30 carbon atoms, R' is methyl or R, a is 1–6, b is 0–5, w is 0–5 and x is 0–5, provided a+b is 3–6 and w is not 0 if R' is methyl. These mixtures form films on the skin which function as barriers to transepidermal water loss and, thus, soften the skin by virtue of its own moisture.

Alkylmethylsiloxane waxes are known in the art for skin care applications. For instance, Th. Goldschmidt AG in their product literature report that certain polysiloxane polyalkylene copolymers known as ABIL ®-WAX 9800 and ABIL ®-WAX 9801 have utility in applications such as day creams, all purpose creams and body lotions. The materials therein are described as soluble in cosmetic oils and waxes and are useful in protecting against aqueous media. The present inventors, however, have discovered that mixtures comprising alkylmethylsiloxane waxes with alkylmethylsiloxane solvents penetrate the skin faster, are more substantive to the skin surface, have improved aesthetics and spreading, and form more occlusive films on the skin than the waxes in conventional solvents.

U.S. Pat. No. 4,574,082 issued Mar. 4, 1986, describes cosmetic moisturizers containing dimethylpolysiloxanes in admixture with organopolysiloxanes such as polymethyloctylsiloxane and polymethyloctadecylsiloxane. This reference, however, is limited to dimethylpolysiloxane solvents which the present inventors have shown are less effective than the alkylmethylsiloxane solvents claimed herein.

Protective skin creams containing hydrocarbon substituted organosiloxanes are also described in United Kingdom Patent No. 737,134 granted Sep. 21, 1955. This reference, however, claims compounds in which the hydrocarbon radicals are at the end of the polymer chain rather than along its backbone. Moreover, this reference also fails to describe the incorporation of alkylmethylsiloxane solvents as in the present invention.

U.S. patent application Ser. No. 07/642,623 filed Jan. 17, 1991 and assigned to the same assignee hereof also discloses alkylmethylsiloxanes for skin care. The application, however, fails to describe the incorporation of alkylmethylsiloxane solvents as claimed and disclosed herein.

Krzysik in U.S. Pat. No. 4,973,476 describes mixtures of a functional siloxane (which may be an alkylmethylsiloxane) and a volatile siloxane (which may be an alkylmethylsiloxane). Such mixtures, however, are described therein as being useful for hair conditioning.

Accordingly novel skin care formulations and methods are provided herein in which alkylmethylsiloxane waxes are mixed with alkylmethylsiloxane solvents and applied to the skin as moisturizing agents.

SUMMARY OF THE INVENTION

The present invention is directed to novel skin care formulations. The novelty herein resides in the inclusion of alkylmethylsiloxane mixtures comprising an alkylmethylsiloxane solvent of the structure [MeRSiO]$_a$[Me$_2$SiO]$_b$ or R'Me$_2$SiO(MeRSiO)$_w$(Me$_2$SiO)$_x$SiR'Me$_2$ and an alkylmethylsiloxane wax of the structure R'Me$_2$SiO(Me$_2$SiO)$_y$(MeRSiO)$_z$SiMe$_2$R', wherein each R is independently a hydrocarbon of 6 to 30 carbon atoms, R' is methyl or R, a is 1–6, b is 0–5, w is 0–5 and x is 0–5, provided a+b is 3–6 and w is not 0 if R' is methyl.

The present invention is also directed to a method of treating human skin to decrease transepidermal water loss and, thereby, soften the skin with its own moisture. The method comprises applying the above novel film forming conditioning mixture to the skin to create a barrier film which inhibits water loss.

These and other features, objects and advantages of the present invention will be apparent upon consideration of the following detailed description of the invention.

DETAILED DESCRIPTION OF THE INVENTION

The present invention is based on the discovery that formulations comprising alkylmethylsiloxane waxes dissolved in alkylmethylsiloxane solvents are unexpectedly superior in skin care applications than alkylmethylsiloxane waxes in known solvents. For instance, the present inventors have shown that the alkylmethylsiloxane solvents herein increase the penetration of the wax, provide a more substantive feel to the skin surface, improve the aesthetics and spreading of the formulation, and enhance the occlusivity of the mixture.

Dry skin symptoms such as scaling and cracking are a common medical problem. Such symptoms often develop when the water content of the outer layers of the stratum corneum of human skin falls below about ten to twenty percent. This problem is most prevalent in very dry environments where the water loss from the external skin layers can be significant. To counteract this problem, water is diffused from the deep layers of the epidermis to the stratum corneum by a concentration gradient. However, since this water too can be quickly lost to the environment, the net moisturizing effect is often minimal.

One method of treating dry skin is to place an occlusive barrier onto the surface of the skin to retard the water loss to the environment and allow the skin surface to rehydrate by diffusion. The present mixture has been shown to provide such a barrier.

The mixtures herein comprise one or more alkylmethylsiloxane solvents. These solvents can be either cyclic having a structure comprising

[MeRSiO]$_a$[Me$_2$SiO]$_b$   (I)

or linear having a structure comprising

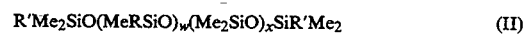

R'Me$_2$SiO(MeRSiO)$_w$(Me$_2$SiO)$_x$SiR'Me$_2$   (II)

wherein each R is independently a hydrocarbon of 6 to 30 carbon atoms, R' is methyl or R, a is 1–6, b is 0–5, w is 0–5 and x is 0–5, provided a+b is 3–6 and b is not 0 if R' is methyl. Exemplary compounds include [MeC$_6$H$_{13}$SiO]$_4$, [MeC$_{14}$H$_{29}$SiO]$_4$, [Me$_2$SiO]$_3$[C$_{18}$H$_{37}$MeSiO]$_1$ and Me$_3$SiO(MeC$_6$H$_{13}$SiO)SiMe$_3$. These solvents may be either volatile or non-volatile and they can have a wide range of viscosities such as from about 0.65 to about 50,000 centistokes.

The siloxane solvent is included in the formulation of this invention in an amount which provides the desired properties (e.g., viscosity) to the mixture. Generally, however, enough solvent should be present so that the solvent:wax ratio is greater than or equal to about 1:1. Though the total amount of solvent in any formulation will vary depending on additional components present, generally, it will comprise between about 20 and about 90 weight percent of the final formulation.

The mixtures of the invention also include alkylmethylsiloxane waxes of the structure

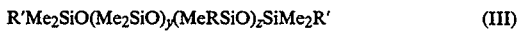

$$R'Me_2SiO(Me_2SiO)_y(MeRSiO)_zSiMe_2R' \quad (III)$$

wherein y is 0–100, z is 1–100, R is an alkyl group of 6–30 carbon atoms and R' is methyl or R. Preferably, the alkylmethylsiloxane has the formula

$$Me_3SiO[Me_2SiO]_y[MeRSiO]_zSiMe_3 \quad (IV)$$

Exemplary alkylmethylsiloxane waxes which are useful herein include $Me_3SiO[Me_2SiO]_3[MeC_{18}H_{37}SiO]_5SiMe_3$, $Me_3SiO[Me_2SiO]_3[MeC_{24}H_{49}SiO]_5SiMe_3$, $Me_3SiO[Me_2SiO]_{70}[MeC_{30}H_{61}SiO]_{30}SiMe_3$, and $Me_3SiO[MeC_{18}H_{37}SiO]_{10}SiMe_3$.

The siloxane wax is included in the mixture of the invention in an amount sufficient to form the desired occlusive film. Though this amount will vary depending on additional components present, generally, it will comprise between about 1 and about 50 weight percent of the final formulation.

The above alkylmethylsiloxane solvents and waxes are known in the art and can be produced by known methods. For example, cyclic alkylmethylsiloxane polymers can be produced by the reaction of a cyclic siloxane having Si-H functional units thereon (e.g., $[MeHSiO]_a$) with a slight stoichiometric excess of an alkene in the presence of a platinum on carbon catalyst. Likewise, linear and cyclic alkylmethyl-dimethyl copolymers can be produced by the reaction of a linear siloxane having Si-H functionality in the chain such as $(Me_3SiO_{0.5})_2(MeHSiO)_x$, in which x is about 4–100, and a cyclic siloxane having $(Me_2SiO)_x$ units, in which x is 3–6. The reaction product (generally about 10% cyclic and 90% linear) is then contacted with a slight stoichiometric excess of an alkene in the presence of a platinum on carbon catalyst.

Batch production of the alkylmethylsiloxanes is conducted by adding the reaction product to a non-agitated suspension of the catalyst in the alkene at about sixty degrees Centigrade. Continuous production of the alkylmethylsiloxanes is conducted by pumping a preheated solution of a stoichiometric excess of an alkene $CH_2=CHR$ and the reaction product through a packed column containing platinum on carbon catalyst chips. The column will require provision for the removal of heat because of the exothermic nature of the reaction.

The materials are further processed in accordance with the present invention in order to provide a more cosmetically acceptable product by removing from the product any remaining cyclic siloxane and any residual methylhydrogendimethylsiloxane cocyclics present as $(MeHSiO)(Me_2SiO)_3$. The alkylmethylsiloxanes produced in accordance with the present invention have been found to contain at most about 0.5 percent residual alkene and about 99.5 percent alkylmethylsiloxane product. No measurable residual amount of platinum has been detected.

The mixtures herein are made by merely mixing the solvent and the wax by conventional techniques. The resultant product is white, odorless, and stable. The products are particularly adapted to skin care in that the materials have been found to form films on the skin which possess a very low water vapor permeability enabling the materials to form a barrier on the skin which will reduce moisture loss from the stratum corneum. In addition, use of the alkylmethylsiloxane solvent has been shown to increase penetration of the wax and improve its aesthetics and its spreadability. Finally, use of the mixture also has been shown to enhance the substantivity of the wax relative to other formulations of said compounds.

The mixtures of the present invention are useful in skin creams and lotions including facial products such as cleaners and moisturizers, hand creams, baby creams and sun care creams and lotions. The mixtures herein may be used in solutions, emulsions, microemulsions, dispersions, lotions, gels, aerosols, solid stick products, ointments, creams and the like.

The above skin care formulations may optionally contain other emollients, sunscreens, and adjuvants such as perfumes, fragrances and preservatives. Examples of other emollients and moisturizers which may be included in compositions of this invention include straight, branched or cyclic hydroxy compounds such as alcohols containing 1 to 30 carbon atoms; straight, branched or cyclic carboxylic acids containing 1 to 31 carbon atoms; acid esters containing $C_1$ to $C_{30}$ carboxylic acids esterfied with $C_1$ to $C_{30}$ alcohols; alcohol ethers containing 1 to 30 carbon atoms; and alkanes of the formula $H-(CH_2)n-H$ wherein n is 5 to 30. Examples of such materials include 2-ethylhexyl oxystearate; arachidyl propionate; 2-ethylhexyl adipate; isopropyl myristate; stearyl alcohol; propylene glycol; propionic acid; stearic acid; polyoxypropylene cetyl alcohol; polyoxypropylene lanolin alcohol; Carbowax® 300; petroleum jelly; mineral oil; aliphatic hydrocarbons such as mineral spirits; lanolin and lanolin derivatives such as acetylated lanolin and isopropyl lanolate.

Sunscreens may also be employed in the formulations of this invention. These include those which absorb ultraviolet light between about 290–320 nanometers (the UV-B region) such as paraaminobenzoic acid derivatives and cinnamates such as octyl methoxycinnamate and those which absorb ultraviolet light in the range of 320–400 nanometers (the UV-A region) such as benzophenones and butyl methoxy dibenzoylmethane. Some additional examples of sunscreen chemicals which may be employed in accordance with the present invention are 2-ethoxyethyl p-methoxycinnamate; menthyl anthranilate; homomenthyl salicylate; glyceryl p-aminobenzoate; isobutyl p-aminobenzoate; isoamyl p-dimethylaminobenzoate; 2-hydroxy-4-methoxybenzophenone-5-sulfonic acid; 2,2'-dihydroxy-4-methoxybenzophenone; 2-hydroxy-4-methoxybenzophenone; 4-mono and 4-bis(3-hydroxypropyl)amino isomers of ethyl benzoate; and 2-ethylhexyl p-dimethylaminobenzoate.

Solvents other than the alkylmethylsiloxanes may also be included in these formulations. These include aliphatic hydrocarbons such as isoparaffins and volatile cyclic dimethylsiloxanes of the formula $[(CH_3)_2(SiO)]_x$ wherein x is four or five and including mixtures of octamethylcyclotetrasiloxane and decamethylcyclopentasiloxane. Such materials have viscosities of less than five centistokes measured at twenty-five degrees Centigrade. These solvent materials provide a non-cooling and nonstinging solvent like characteristic and evaporate leaving little or no residue. The solvent can also be any aliphatic alcohol such as isopropyl alcohol or ethyl alcohol, esters such as isopropyl myristate and other volatile solvents such as ethyl acetate. It should be noted however that the solvent must be compatible with and capable of dissolving the alkylmethyl polysiloxane as well as any added optional components of the formulation.

It should be apparent from the foregoing that many other variations and modifications may be made in the compounds, compositions and methods described herein without departing substantially from the essential features and concepts of the present invention. Accordingly it should be clearly understood that the forms of the invention described herein are exemplary only and are not intended as limitations on the scope of the present invention as defined in the appended claims.

The following non-limiting examples are provided so that one skilled in the art will more readily understand the invention.

EXAMPLE 1

In order to illustrate the durability of the mixtures of this invention relative to linear alkylmethyl siloxanes in other solvents known in the art, data was collected by employing a soap washing procedure that involved the measurement of substantivity on human skin. The amount of test solution on the skin before and after the wash was measured by Attenuated Total Reflectance/Fourier Transform Infrared Spectrophotometric (ATR/FTIR) analysis in which skin studies were conducted and analyzed based on the reflection of energy at the prism/skin interface. Instrumentation included a NICOLET model 20DX FTIR system and a HARRICK Scientific Skin Analyzer. The ATR studies involved contact of the skin sample and prism. Baselines for infrared bands were defined and band heights were measured (initial test). The percent ingredient remaining on the skin was calculated using these data.

The method of testing comprised diluting an alkylmethyl siloxane of the structure $Me_3SiO(C_{18}H_{37}MeSiO)_{10}SiMe_3$ to 10% by weight in (A) ISOPAR G (C10-11 Isoparafin (branched chain aliphatic hydrocarbons with 10–11 carbon atoms in the hydrocarbon chain))-(comparative), (B) cyclic polydimethyl siloxanes comprising a mixture of tetramer and pentamer and having a viscosity of about 2.5 centistokes measured at twenty-five degrees Centigrade (comparative) and (C) an alkylmethylsiloxane of this invention comprising $(Me_3SiO)_2MeSiC_6H_{13}$. The diluted solution was then applied to the skin in the following manner:

The softness and flexibility of the skin test site (about 80 square centimeters of the volar forearm) was initially increased by a hydration procedure so that contact between the skin and instrumentation was reliable. This hydration comprised holding a towel saturated with water loosely over the test area for 1 minute. Excess moisture was blotted and a background scan was run. About eight to ten milligrams of the test solution was then applied to the skin test site in the form of a thin film using a small paint brush. The solvent was allowed to evaporate for fifteen to thirty minutes and the skin was again hydrated for one minute and excess moisture blotted off. A scan of the initial condition of the test are was run.

The test area was then washed with a 0.5 weight percent solution of IVORY® bar soap cupped in the palm of the hand and passed over the test area two times. One soap wash procedure included fifteen soap rubs and ten rinse rubs under cool running tap water. After one minute the skin was hydrated for one minute, blotted and a scan was run of the test area (First Soap Wash Condition). Similar steps were repeated for the second and third soap wash conditions.

Table I indicates the substantivity results obtained. The results show that the alkylmethylsiloxane mixture of the present invention as represented by sample (C) is more durable than comparative samples (A) and (B).

TABLE I

| | Percent Remaining on Skin After Wash | | |
|---|---|---|---|
| Wash Number | Sample (A) | Sample (B) | Sample (C) |
| 1 | 48.5 | 78.0 | 86.2 |
| 2 | 34.7 | 56.6 | 81.1 |
| 3 | 32.3 | 45.3 | 59.7 |

EXAMPLE 2

The occlusive film forming ability of the mixtures of the present invention was demonstrated by conducting measurements of transepidermal water loss by employing an in vitro water vapor permeability test. The test method was as follows:

Payne stainless steel permeability cups were charged with 3 mL of water. A layer of collagen was then placed over the cups and a thin film of the test material spread across the collagen. The cups were placed in an oven at low humidity and skin temperature. Weight loss measurements were taken over time to obtain water loss rates.

The compositions tested in this experiment comprised (A) a mixture of $(Me_3SiO)_2MeSiC_6H_{13}$ and $Me_3SiO(Me_2SiO)_{70}(C_{30}H_{61}MeSiO)_{30}SiMe_3$ (B) a mixture of $(C_6H_{13}MeSiO)_4$ and $Me_3SiO(Me_2SiO)_3(C_{24}H_{49}MeSiO)_5SiMe_3$ and (C) $[Me_2SiO]_3[C_{18}H_{37}MeSiO]_1$ and $Me_3SiO(Me_2SiO)_3(C_{18}H_{37}MeSiO)_5SiMe_3$.

Table II sets forth the weight loss data. These results show that the mixtures of the present invention form an occlusive barrier to transepidermal water

TABLE II

| In vitro Water Vapor Permeability of Alkylmethylsiloxane Mixtures Expressed as g/m²/h | | |
|---|---|---|
| Sample (A) | Sample (B) | Sample (C) |
| 44.2 | 25.3 | 67.8 |

EXAMPLE 3

In order to illustrate the enhanced penetration of the mixtures of this invention relative to linear alkylmethyl siloxanes in other solvents known in the art, the following test was performed. An alkylmethyl siloxane of the structure $Me_3SiO(C_{18}H_{37}MeSiO)_{10}SiMe_3$ was diluted to 10% by weight in (A) cyclic polydimethyl siloxanes comprising a mixture of tetramer and pentamer and having a viscosity of about 2.5 centistokes measured at twenty-five degrees Centigrade (comparative) and (B) a volatile alkylmethylpolysiloxane of this invention comprising $(Me_3SiO)_2MeSiC_6H_{13}$.

Nearly equivalent amounts of the above solutions (A=0.967 g, B=0.1022 g) were then applied to the skin. After 60 minutes, the amount of siloxane remaining on the skin was measured by FTIR/ATR spectroscopy. The amount remaining from solution A=0.468 and the amount remaining from solution B=0.159.

As is readily apparent, incorporation of the alkylmethylsiloxane solvent increased the penetration of the alkylmethylsiloxane wax.

That which is claimed is:

1. In a method of treating human skin to decrease transepidermal water loss by applying a film forming conditioning formulation to the skin, the improvement comprising utilizing a formulation containing a mixture of
   A) an alkylmethylsiloxane solvent selected from the group consisting of $[MeRSiO]_a[Me_2SiO]_b$ or $R'Me_2SiO(MeRSiO)_w(Me_2SiO)_xSiR'Me_2$ and
   B) an alkylmethylsiloxane wax of the structure $R'Me_2SiO(Me_2SiO)_y(MeRSiO)_zSiMe_2R'$,
   wherein each R is independently a hydrocarbon of 6 to 30 carbon atoms, R' is methyl or R, a is 1-6, b is 0-5, w is 0-5, x is 0-5, y is 0-100 and z is 1-100, provided a+b is 3-6 and w is not 0 if R is methyl.

2. The method of claim 1 wherein the alkylmethylsiloxane wax is of the structure $Me_3SiO(Me_2SiO)_y(MeRSiO)_zSiMe_3$.

3. The method of claim 1 wherein the alkylmethylsiloxane solvent is of the structure $[MeRSiO]_a$, wherein a is 4.

4. In a film forming conditioning formulation for the treatment of human skin to decrease transepidermal water loss, the improvement comprising the incorporation of a mixture containing
   A) an alkylmethylsiloxane solvent selected from the group consisting of $[MeRSiO]_a[Me_2SiO]_b$ or $R'Me_2SiO(MeRSiO)_w(Me_2SiO)_xSiR'Me_2$ and
   B) an alkylmethylsiloxane wax of the structure $R'Me_2SiO(Me_2SiO)_y(MeRSiO)_zSiMe_2R'$,
   wherein each R is independently a hydrocarbon of 6 to 30 carbon atoms, R' is methyl or R, a is 1-6, b is 0-5, w is 0-5, x is 0-5, y is 0-100 and z is 1-100, provided a+b is 3-6 and w is not 0 if R' is methyl. In the specification:

5. The formulation of claim 4 wherein the alkylmethylsiloxane wax is of the structure $Me_3SiO(Me_2SiO)_y(MeRSiO)_zSiMe_3$.

6. The formulation of claim 1 wherein the alkylmethylsiloxane solvent is of the structure $[MeRSiO]_a$, wherein a is 4.

* * * * *